United States Patent [19]

Gane et al.

[11] Patent Number: 4,565,897

[45] Date of Patent: Jan. 21, 1986

[54] PRODUCTION OF AROMATIC HYDROCARBONS

[75] Inventors: Brian R. Gane, Ottershaw; Antony H. P. Hall, Cobham, both of England

[73] Assignee: The British Petroleum Company p.l.c., London, England

[21] Appl. No.: 681,010

[22] Filed: Dec. 13, 1984

[30] Foreign Application Priority Data

Dec. 24, 1983 [GB] United Kingdom ................ 8334486

[51] Int. Cl.$^4$ ................................................ C07C 2/84
[52] U.S. Cl. ...................................... 585/415; 585/407
[58] Field of Search ................................. 585/415, 407

[56] References Cited

U.S. PATENT DOCUMENTS 4,180,689  12/1979  Daries et al. ........................ 585/415
4,350,835   9/1982  Chester et al. ...................... 585/415

FOREIGN PATENT DOCUMENTS 0050021  4/1982  European Pat. Off. ............ 585/415

Primary Examiner—John Doll
Assistant Examiner—A. Pal
Attorney, Agent, or Firm—Brooks, Haidt, Haffner & Delahunty

[57] ABSTRACT

This invention relates to a process for producing aromatic hydrocarbon from a feedstock comprising $C_3/C_4$ hydrocarbons mixed with $C_2$ hydrocarbons, especially ethane. The mixed feedstock is contacted at a temperature below 580° C. with a catalyst composition comprising an aluminosilicate in which the molar ratio of silica to alumina is at least 5:1.

The product is rich in aromatics and can be used as a gasoline blending component.

11 Claims, No Drawings

PRODUCTION OF AROMATIC HYDROCARBONS

The present invention relates to a process for producing aromatic hydrocarbons from a hydrocarbon feedstock comprising $C_3$ and/or $C_4$ hydrocarbons mixed with $C_2$ hydrocarbons, especially ethane.

Hitherto synthetic routes to producing aromatics from open chain hydrocarbons have started either from feedstocks which have at least three carbon atoms or from feedstocks which contain $C_2$ hydrocarbons as the major component. Feedstocks containing 3 or more carbon atoms are initially dimerised and the dimerised product is subsequently cyclised over a variety of catalysts at elevated temperatures. Such processes are described for example in our British Pat. Nos. 1507778 and 1561590. On the other hand hydrocarbon feedstocks which have a major $C_2$ component have been converted to aromatics at temperatures above 580° C. as claimed and described in our published European patent application No. 0050021. Aromatic hydrocarbons produced in this manner are usually accompanied by small quantities of open chain hydrocarbons and together are useful amongst others as gasoline blending components.

It has now been found that the presence of ethane in the feed has a significant beneficial effect on the selectivity to aromatics obtained on reaction of $C_3/C_4$ hydrocarbons at temperatures significantly below that required for aromatisation of ethane alone.

Accordingly, the present invention is a process for producing aromatic hydrocarbons comprising bringing into contact at a temperature below 580° C. a mixed hydrocarbon feedstock containing at least 50% w/w of $C_3$ and/or $C_4$ hydrocarbons and from 10 to 50% w/w of ethane with a catalyst composition comprising an aluminosilicate in which the molar ratio of silica to alumina is at least 5:1.

The aluminosilicates have a silica to alumina molar ratio above 5:1, suitably from 20:1 to 150:1 and are suitably MFI type zeolites of the general formula: $M_{2/n}O.Al_2O_3.ySiO_2.zH_2O$ wherein M is a cation which is a positively charged ion of valence n, y is an integer greater than 5 and z is from 0 to 40. The cation, M, is preferably an alkali metal ion, an alkaline earth metal ion or a proton. MFI zeolites belong to a class of known zeolite structure types published by The Structure Commission of the International Zeolite Association ("Atlas of Zeolite Structure Types", by Meier, W. M. and Olsen, D. H. (1978), distributed by Polycrystal Book Service, Pittsburgh, Pa., USA). Specific examples of such zeolites are the ZSM varieties especially ZSM-5. These zeolites are usually produced from a silica source, an alumina source, an alkali metal hydroxide and a nitrogen-containing base such as ammonia or an alkanolamine, for example diethanolamine. Zeolites made in this manner are described in our published European patent application Nos. 002899 and 0002900.

The aluminosilicates may be used for the hydrocarbon conversion in the as synthesised form and in the hydrogen form. It is however preferable to load the aluminosilicate with a catalytic component such as a metal compound or a metal ion. Compounds and ions of gallium are particularly preferred. In order to produce a gallium loaded catalyst which has adequate life and activity the as synthesised zeolite is suitably subjected to a series of treatments. The series of treatments may include (a) washing the as synthesised zeolite with a dilute acid e.g. nitric acid;

(b) drying the washed, acid-treated zeolite from (a);

(c) calcining the dried zeolite from (b) at an elevated temperature, e.g. above 500° C.;

(d) loading the calcined zeolite with a gallium compound or gallium ions by well known impregnation or ion-exchange techniques; and (e) binding the gallium loaded zeolite in a binder with a porous matrix such as e.g. silica or alumina.

Catalysts prepared in this manner have a high initial activity but this may decline rapidly because of an accompanying high rate of carbon deposition. However, it has been found that the catalyst can be partially deactivated so that the carbon deposition is significantly reduced with only a small effect on activity. This controlled deactivation may be produced by treating the catalyst with steam or by a high temperature dry calcination.

The steam treatment may be carried out with pure or diluted steam, preferably 10 to 40% vol/vol at temperatures over 400° C., preferably 500° to 650° C. The alternative dry temperature calcination may be carried out at temperatures above 600° C., preferably 700°-900° C. These treatments may, depending upon the method of zeolite preparation, allow the initial calcination step (c) to be eliminated but are normally carried out in addition to the initial calcination.

The as synthesised zeolite after washing, drying and calcination may be loaded with gallium either by exchanging cations in the zeolite with gallium ions or by impregnating the zeolite with a gallium compound.

In the case where the cations in the aluminosilicate have been exchanged for gallium ions, the gallium ion is suitably provided as an aqueous solution of a gallium salt such as for instance gallium nitrate, gallium chloride or gallium sulphate. Such catalysts may be prepared by conventional ion exchange techniques and the catalysts so produced are subsequently dried. For example an aqueous solution of a gallium compound such as gallium nitrate may be placed in contact with the aluminosilicate at ambient or elevated temperature, e.g. by refluxing. The exchanged aluminosilicate is then separated by decantation followed by filtration, washed several times with deionised water and finally dried. Before addition to the aqueous solution of the gallium compound, the aluminosilicate may be treated in the manner described in our published copending European patent application No. 0024930.

Alternatively the gallium loaded zeolite may be produced by conventional impregnation techniques in which a gallium compound e.g. gallium oxide is impregnated on the surface of the aluminosilicate or is incorporated in the intracrystalline zeolite cavities as such or as a gallium compound which gives rise to gallium oxide during activation of the catalyst prior to contact with the hydrocarbon feedstock. An example of a suitable gallium compound is gallium nitrate.

The impregnation may be achieved by preparing a solution, suitably an aqueous solution, of a gallium compound such as for example gallium nitrate and adding a conventional aluminosilicate to this aqueous solution with thorough stirring to form a paste. The paste is subsequently dried at an elevated temperature in vacuum.

Where the catalyst composition is prepared by using a compound of gallium which ionises in aqueous solution, for example gallium nitrate, some of the gallium ions may be exchanged with the cations in the aluminosilicate even if the preparation was by impregnation of the aluminosilicate.

Whichever method of catalyst preparation or activation is used, the amount of gallium present in the catalyst compositions may vary for instance between 0.05 and 10% by weight of the total aluminosilicate in the catalyst composition.

The mixed feedstock contains $C_3$ and/or $C_4$ hydrocarbons, as the major reactant. Specific examples of the $C_3$ and $C_4$ hydrocarbons are propane, propylene, n-butane, isobutane, n-butenes and isobutene. Of these propane and the butanes are the most preferred. The hydrocarbon feedstock suitably contains more than 50%, preferably at least 70% by weight of the $C_3/C_4$ hydrocarbons.

The mixed feedstock which is converted to aromatic hydrocarbons or gasoline blending components suitably contains less than 45% w/w of ethane, preferably from 15–45% w/w of ethane.

Ethane may be added to the $C_3/C_4$ components from an external source or as a recycled product generated during the aromatisation of $C_3/C_4$ feedstock. This technique of recycling ethane is especially preferable in a continuous process which, after an initial induction period, generates sufficient ethane for a steady state to be achieved while removing excess ethane with the methane by-product.

The process is suitably a gas phase process and the conversion of the mixed feedstock to aromatics and/or aromatic containing gasoline blending components is suitably carried out at a temperature above 450° C., preferably from 475°–575° C.

Reaction pressures used are suitably from 1–20 bar, preferably from 2–10 bar.

The mixed feedstock is suitably brought into contact with the catalyst composition for a duration of 1–50 seconds, preferably from 5–20 seconds. The LHSV of the reactants is suitably from 0.5–8, preferably from 2–4.

The mixed ethane containing-feedstock of the present invention gives results that are better than would be expected from combining the results obtained with the single feeds, and the addition of ethane has a beneficial effect that is not observed on diluting the feed with nitrogen (i.e. the effect is not simply caused by the reduction of partial pressures of reactants and products).

The process of the present invention is further illustrated with reference to the following Examples.

EXAMPLE 1

Catalyst Details

The zeolite was prepared using the diethanolamine method described in our published European specification Nos. 002899 and 002900 and had a $SiO_2:Al_2O_3$ molar ratio of 39.6:1.

The zeolite was washed with dilute nitric acid, dried under vacuum, and calcined at 550° C. for 60 hours. The calcined material was refluxed with gallium nitrate solution, filtered, washed and dried. It was then bound with sufficient Ludox AS 40 (Regd. Trade Mark) to give granules containing 25% binder. The bound catalyst was treated with 19% vol/vol steam in air at 550° C. for 2 hours prior to loading with gallium oxide as described in our published European Pat. No. 0024930.

A mixture containing by weight 54% of propane, 4.5% butane and 41.5% ethane was passed over a gallium/zeolite catalyst, containing 0.6% wt gallium, maintained at 535° C. and 6 bar absolute pressure. The contact time, calculated at reaction condition, was approximately 14 seconds. Over several periods, during a total of 98 hours on stream, samples of the liquid and gaseous products were collected and analysed. The average of these test periods gave yields of 28.5% wt of liquid, which contained over 95% aromatics, with recoveries of propane and butane of 7.8% and 0.3% respectively. The total ethane concentration in the product was higher than that in the feed. The liquid may therefore be considered to have resulted from the conversion of 46.2% propane and 4.2% butane, which represents a selectivity of 56.5% by weight.

In contrast, a feed containing 91.7% wt propane and 7.5% butane gave a 37.2% wt yield of liquid over 97 hours with the same catalyst and reaction conditions. The recoveries of propane and butane were 20.0% and 0.2% respectively, giving a selectivity of 47.0% by weight.

With ethane alone as feed a liquid yield of 2.5% wt was obtained under the same conditions. The mixed feed described above may therefore have been expected to give only 24.7% liquid, made up from 1.0% produced from ethane and 23.7 from the conversion of 50.4% propane and butane at 47% selectivity which is significantly less than that actually achieved.

EXAMPLE 2

Comparison of Ethane and Nitrogen Additives

With the same feed mixture and reaction conditions as described in Example 1 the weight of liquid obtained over a two hour test period was equivalent to 46.3% of the propane and butane in the feed. $C_3$ and $C_4$ hydrocarbons, including traces of olefins, were recovered in a quantity equivalent to 20.6% of the feed. The resulting selectivity to liquid was therefore 58.3% by weight.

The ethane in the feed was then largely replaced by nitrogen. Over another two hour period the liquid obtained was equivalent to 39.4% of the propane and butane in the feed and the recovery of $C_3$ and $C_4$ hydrocarbons was 17.0%. The resulting selectivity to liquids was therefore 47.5% by weight.

We claim:

1. A process for producing aromatic hydrocarbons comprising bringing into contact at a temperature below 580° C. a mixed hydrocarbon feedstock containing at least 50% w/w of $C_3$ and/or $C_4$ hydrocarbons and from 10 to 50% w/w of ethane with a catalyst composition comprising an aluminosilicate in which the molar ratio of silica to alumina is at least 5:1.

2. A process according to claim 1 wherein the aluminosilicate is in the as synthesised form, or the hydrogen form or is loaded with a metal compound or a metal ion.

3. A process according to claim 2 wherein the metal in the metal compound or metal ion is gallium, and wherein the hydrocarbon feedstock is at least 50% w/w of $C_3$ and $C_4$ hydrocarbons and from 10 to 50% w/w of ethane.

4. A process according to claim 1 or 2 wherein the hydrocarbon feedstock contains more than 50% w/w of $C_3$ and/or $C_4$ hydrocarbons and less than 45% w/w of ethane.

5. A process according to claim 1 wherein the molar ratio of silica to alumina in the gallium loaded aluminosilicate is from 20:1 to 150:1.

6. A process according to claim 3 wherein the catalyst composition has a gallium content of 0.05 to 10% w/w of the total aluminosilicate in said composition.

7. A process according to claim 1 wherein conversion of the mixed hydrocarbon feedstock to aromatics and/or gasoline blending components is carried out in the gas phase at a temperature from 475° to 575° C.

8. A process according to claim 1 wherein conversion of the mixed hydrocarbon feedstock is carried out at a pressure from 1 to 20 bar absolute.

9. A process according to claim 1 wherein the catalyst composition is partially deactivated by treatment with steam or by high temperature dry calcination prior to contact with the mixed hydrocarbon feedstock.

10. A process according to claim 1 or claim 2 wherein ethane is added to the $C_3/C_4$ components from an external source or as a recycled product generated during the aromatisation of $C_3/C_4$ feedstock.

11. A process according to claim 10 wherein the ethane added is a recycled product generated during the aromatisation of $C_3/C_4$ feedstock.

* * * * *